United States Patent [19]

Lerner et al.

[11] Patent Number: 5,250,426

[45] Date of Patent: Oct. 5, 1993

[54] MOLECULES WITH ANTIBODY COMBINING SITES THAT INDUCE ASYMMETRY

[75] Inventors: Richard A. Lerner, La Jolla; Kim Janda, San Diego, both of Calif.

[73] Assignee: The Scripps Research Institute, La Jolla, Calif.

[21] Appl. No.: 781,720

[22] Filed: Oct. 22, 1991

[51] Int. Cl.$^5$ .............................. C12P 7/42; C12N 9/00
[52] U.S. Cl. ................... 435/146; 435/188.5; 435/197; 435/240.27; 530/388.9
[58] Field of Search ............... 435/188.5, 240.27, 146, 435/197; 430/388.9

[56] References Cited

U.S. PATENT DOCUMENTS

| | | | |
|---|---|---|---|
| 4,342,566 | 2/1980 | Theofilopoulos et al. | 422/57 |
| 4,361,549 | 11/1982 | Kung et al. | 424/85 |
| 4,659,567 | 4/1987 | Tramontano et al. | 424/85 |
| 4,792,446 | 12/1988 | Kim et al. | 424/85 |
| 4,888,281 | 12/1989 | Schochetmann et al. | 435/72 |
| 5,030,717 | 7/1991 | Tramontano et al. | 530/387 |
| 5,156,965 | 10/1992 | Schochetman et al. | 435/188.5 |

OTHER PUBLICATIONS

Blackburn, G. M., et al., (1989), Biochem. J., 262, 381–390.
Lerner, R. A., et al., (1988), Bioassays, 9, 107–112.
Pollack, S. J., et al., (1989), J. Am. Chem. Soc., 111, 5961–5962.
Janda, K. D., et al., (1989), Science, 244, 437–440.
Slobin, Biochemistry, 5:2836–2844 (1966).
Kohnen et al., FEBS Letters, 100:137–140 (1979).
Kohnen et al., Biochim. Biophys. Acta, 629:328–337 (1980).
Kohnen et al., FEBS Letters, 111:427–431 (1980).
Jencks, W. P., Catalysis in Chemistry and Enzymology, pp. 287–289 (McGraw-Hill, New York, 1969).
Lerner, Tramontano and Janda, Science, 234, 1566 (1986).
Pollack, Jacobs and Schultz, Science, 234, 1570 (1986).
Leon et al., Biochem., 10, 1424 (1971).
Jacobs et al., J. Am. Chem. Soc., 109, 2174 (1987).
Benkovic et al., Proc. Natl. Acad. Sci. USA, 85:5355 (1988).
Jackson et al., J. Am. Chem. Soc., 110:4841 (1988).
Napper et al., Science, 237:1041 (1987).
Hilvert et al., Proc. Natl. Acad. Sci. USA, 85:4953 (1988).
Jencks, W. P., Adv. Enzymology, 43, 219 (1975).
Pauling, L., Amer. Scientist, 36, 51 (1948).
Leinhard, G., Science, 180, 149 (1973).
Wolfenden, R., Acc. Chem. Res., 5, 10 (1972).
Jencks, W. P., XVII International Solvay Conference, (Nov. 1983), 2190.
Kohler and Milstein, Nature, 256, 495 (1975).
Bartlett, et al., Biochemistry, 22, 4618 (1983).
W. P. Jencks, Catalysis in Chemistry and Enzymology, ch. 10, (McGraw-Hill, New York, 1969).
Westerik et al., J. Biol. Chem., 247, 8195 (1972).
R. C. Thompson, Biochemistry, 12, 47 (1973).
Imperali et al., Biochemistry, 25, 3760 (1986).
Weaver et al., J. Mol. Biol., 114, 119 (1977).
Jacobson et al., J. Am. Chem. Soc., 103, 654 (1981).
W. N. Lipscomb, Acc. Chem. Res., 15, 232 (1982).

(List continued on next page.)

Primary Examiner—Charles L. Patterson, Jr.
Attorney, Agent, or Firm—Dressler, Goldsmith, Shore, Sutker & Milnamow, Ltd.

[57] ABSTRACT

Monoclonal antibodies or paratope-containing portions thereof are disclosed that immunoreact with an enol ester substrate ligand having a prochiral center and catalytically hydrolyze a single predetermined ester bond to form a product that contains relatively more of one of a pair of enantiomers than the other enantiomer. Methods of making and using the same are also disclosed.

8 Claims, No Drawings

OTHER PUBLICATIONS

Christianson et al., *J. Am. Chem. Soc.*, 108, 545 (1986).
L. M. Sayre, *J. Am. Chem. Soc.*, 108, 1632 (1986).
Liu et al., *Biochem.*, 80, 690 (1979).
Niman et al., *Proc. Natl. Acad. Sci. USA*, 77, 4524 (1980).
Niman et al., *Monoclonal Antibodies and T-Cell Products*, Katz, D. M. ed., 23-51, CRC Press, Boca Raton, Fla. (1982).
Shulman et al., *Nature*, 276, 269 (1978).
Galfre et al., *Nature*, 277, 131 (1979).
Goding, "Production of Monoclonal Antibodies by Cell Fusion", in *Antibody as a Tool*, Marchalonis et al., eds., John Wiley & Sons Ltd., p. 273 (1982).
Engvall, E., *Methods Enzymol.*, 70, 419 (1980).
Stedman et al., *Biochem. J.*, 26:2056 (1932).
Alles et al., *Biol. Chem.*, 133: 375 (1940).
Laemmli, V., *Nature*, 227: 680 (1970).
Neuberger et al., *Nature*, 312:604–608 (1984).
Ochi et al., *Proc. Natl. Acad. Sci. USA*, 80:6351-55 (1983).
Oi et al., *Proc. Natl. Acad. Sci. USA*, 80:825-29 (1983).
Wood et al., *Nature*, 314:446-9 (1985).
Janda et al., *Tetrahedron*, 47:2503-2506 (1991).

MOLECULES WITH ANTIBODY COMBINING SITES THAT INDUCE ASYMMETRY

This invention was made with government support under Contract GM 43858 awarded by the National Institutes of Health. The government has certain rights in the invention.

DESCRIPTION

1. Technical Field

The present invention relates to antibodies, antigens and immunogens, and more particularly to paratope-containing molecules that catalyze the hydrolysis of a preselected prochiral carboxylic ester bond and induce asymmetry by that hydrolysis.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, *Biochemistry*, 5:2836-2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohnen and coworkers also reported attempts using antibodies to catalyze esterolysis. The antibodies utilized by this group were, in each instance, raised to a portion of the ultimately utilized substrate molecule that did not contain the bond to be hydrolyzed.

In their initial work [FEBS Letters, 100:137-140 (1979) and Biochim. Biophys. Acta. 629:328-337 (1980)] anti-steroid antibodies were used to hydrolyze 7-umbelliferone (7-hydroxycoumerin) esters of a carboxyethyl thioether of a steroid. In each instance, an increase in hydrolytic rate was observed as compared to background or to a rate obtained with normal IgG. In both instances, turn over numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolysis of 7-[-N-(2,4-dinitrophenyl)-6-aminohexanoyl]-coumerin using monoclonal antibodies raised to the dinitrophenyl portions of that substrate molecule [*FEBS Letters*, 111:427-431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex will impede catalysis Such is thought to be the situation for the results reported by Kohnen and coworkers.

The above constructs, though interesting, are severely limited by the failure to address the mechanism of binding energy utilization which is essential to enzymes [W. P. Jencks, Adv. Enzymol., 43, 219 (1975)].

Those deficiencies can be redressed by using a transition state analog as the hapten to elicit the desired antibodies. This hapten (also referred to herein as an "analog-ligand") can assume the role of an inhibitor in the catalytic system.

Thus, immunological binding can be used to experimentally divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymoloy*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states cannot be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood.

It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity, i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the translation product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [*Science*, 234, 1566 (1986)] reported monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrate and analog substrate system for carbonate hydrolysis similar in concept to that of Lerner et al. Work relating to that system is reported in Jacobs et al., *J. Am. Chem Soc.*, 109, 2174 (1987).

U.S. Pat. No. 4,888,281 (Schochetman et al.) discusses the possible use of antibodies as catalysts, and presents data relating to the use of polyclonal serum in hydrolyzing o-nitrophenyl-beta-D-galactoside. The antibodies useful in that patent are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. The patent did indicate that beta-D-galactosidase cleaved about ten times as much substrate as did the polyclonal antibodies, presuming linearity of absorbance at the unnamed concentration of substrate studied.

From the data presented in that patent, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 (Kim et al.) discusses the possible use of antibody catalysts in the synthesis of chiral molecules. However, such syntheses were neither described nor disclosed in that patent.

In more recent work, bimolecular amide formation catalyzed by antibody molecules has been disclosed [Benkovic et al., *Proc. Natl. Acad. Sci. USA*, 85:5355 (1988)], as has an antibody-catalyzed Claisen rearrangement [Jackson et al., *J. Am. Chem. Soc.*, 110:4841 (1988)]. None of that work, nor the previously discussed work, has contemplated the use of antibodies to catalyze any reaction in a stereospecific manner.

Stereospecificity was shown in an antibody-catalyzed lactone-forming reaction [Napper et al., *Science*, 237:1041 (1987)] and in an antibody-catalyzed Claisen reaction [Hilvert et al., *Proc. Natl. Acad. Sci. USA*, 85:4955 (1988)]. The use of paratope-containing molecule to catalyze a hydrolysis reaction of a meso compound to yield a product that is one of a pair of enantiomers as is described hereinafter was not, however, contemplated in any of the above publications.

BRIEF SUMMARY OF THE INVENTION

The present invention contemplates a receptor molecule that contains an antibody combining site or paratope-containing polyamide that catalytically hydrolyzes a preselected, scissile enol carboxylic acid ester bond of a prochiral substrate enol ester reactant ligand. That antibody combining site binds to (immunoreacts with):
(a) A substrate enol carboxylic acid ester reactant ligand containing that preselected scissile enol carboxylic acid ester bond and an enol ester compound nucleus containing at least 5 carbon atoms, and (b) an analog-ligand that contains a tetrahedrally bonded phosphorus atom at a position analogous to that of the carbonyl carbon atom of the preselected scissile enol carboxylic acid ester bond of the substrate and carboxylic acid ester reactant ligand. The hydrolytic transition state of the substrate enol carboxylic acid ester reactant ligand so bound contains a tetrahedral carbon atom bonded to (i) a carbon atom, the alpha carbon of the acid portion of the ester, (ii) two oxygen atoms, and (iii) the oxygen atom of an ester.

Molecules containing an antibody combining site that bind to the hydrolytic transition state of a substrate enol carboxylic acid ester reactant ligand are raised or induced by immunizing with an analog-ligand molecule (preferably bound to a protein carrier to form a conjugate) that contains an analog of a hydrolytic transition state of the substrate ligand. The immunizing analog-ligand hydrolytic transition state molecule contains a tetrahedrally bonded phosphorus atom, bonded directly to (i) a carbon atom of a carboxylic acid portion of the analogous enol carboxylic acid ester reactant ligand (the alpha-carbon of the acid portion), (ii) two oxygen atoms, and (iii) a third oxygen atom that is bonded to a carbon atom of the alcohol portion of the analogous substrate ligand (the alpha-carbon of the alcohol portion).

The alpha-carbon atom of the acid portion, (i) above, bonded directly to the central tetrahedral phosphorus atom of the analog-ligand molecule, is included in a radical that contains one to about 10 carbon atoms, and more preferably contains 6 to about 10 carbon atoms and associated hydrogens. Of the two oxygen atoms [(ii) above] bonded directly to the central phosphorus atom, one oxygen atom is bonded twice (doubly bonded). The second of those oxygen atoms bonded to the central atom is singly bonded to the central phosphorus atom and is also bonded to a hydrogen, a $C_1$-$C_4$ alkyl or benzyl radical or is an oxy group (0.) neutralized by an alkali metal cation. The fourth atom, (iii) above, bonded to the central phosphorus atom of the analog-ligand molecule corresponds to the alcohol oxygen atom of an ester of the analogous ester portion of the ligand. That fourth atom (third oxygen) is also bonded to a radical that contains at least five carbon atoms, and more preferably contains 6 to about 10 carbon atoms along with attendant hydrogen atoms. At least one of the alcohol and carboxylic acid portions of the enol carboxylic acid ester substrate ligand and corresponding analog-ligand contains at least five carbon atoms in a ring structure.

It is emphasized that the substrate enol ester compound contains at least one carbon atom that can exist in two stereoisomeric forms, and thereby provides a potential stereoisomeric center. That potential stereoisomeric center is located in the substrate enol ester compound molecule at the $\beta$-carbon of the enolic saturation. The potential stereoisomeric center is also located near enough to the bond to be hydrolyzed so that the potential stereoisomeric center is bound by the catalytic antibody combining site-containing molecule.

The tetrahedrally bonded central atom is phosphorus of a phosphonate group so that the analog-ligand is an organophosphorus compound with an arrangement of substituents about the phosphorus atom that corresponds to the tetrahedral carbon transition state for ester hydrolysis of the enol ester substrate ligand. A phosphonate monoacid in its ionized form also simulates the developing charge in nucleophilic attack at a carbonyl center.

In the studies described herein, phosphonate esters function as transition state analogs to induce antibodies that are monoclonal and that are asymmetry-inducing carboxylic esterases. In effect, these antibodies express their inherent binding energy functionally, as true enzymes, to catalytically hydrolyze esters, and classically, as antibodies, to bind antigens.

An enol carboxylic acid ester substrate ligand can be expressed by structural formula I as:

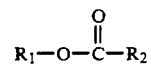

wherein
$R_1$ is an alkenyl or cycloalkenyl group containing at least 5 carbon atoms and a prochiral center, and more preferably 6 to about 10 carbon atoms and attendant hydrogen atoms, with the $\alpha$-carbon atom of the ethylenic unsaturation bonded directly to the oxygen atom of the illustrated ester linkage, thereby constituting the enolic portion of the ester, and the $\beta$-carbon of the ethylenic unsaturation bonded to a $C_1$-$C_6$ alkyl group defining the $\beta$-carbon as the prochiral center;
$R_2$ is an alkyl, aralkyl or aromatic radical containing at least 1 carbon atom, and more preferably 6 to about 10 carbon atoms and attendant hydrogen atoms; and
at least one of $R_1$ and $R_2$ contains a ring structure having five to seven carbon atoms in the ring.

A corresponding analog-ligand can therefore be expressed by structural Formula II as:

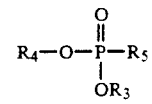

wherein $R_4$ is structurally analogous to $R_1$ except that $R_4$ is saturated at positions analogous to the enolic unsaturation of $R_1$, and $R_4$ is bonded to the phosphonate ester oxygen at a position isomeric to the $\alpha$-carbon atom of the R enolic saturation, but within 2 carbon atoms thereof;
$R_5$ is structurally analogous to $R_2$, except that an $R_5$ group of an analog-ligand further includes a group or radical through which a haptenic analog-ligand can be linked to an antigenic carrier for purposes of immunization, as noted hereinafter; and
$R_3$ is H (hydrogen), $C_1$-$C_4$ alkyl or an alkali metal salt.

A method of preparing monoclonal receptor molecules that bind to the hydrolytic transition state of a particular ester is also contemplated. Here, a before-described haptenic analog-ligand molecule containing a hydrolytic transition state analog is provided linked to a carrier as an immunogenic conjugate. The conjugate thus provided is dissolved or dispersed in a physiologically tolerably diluent to form an inoculum. The inoculum is introduced as by injection into a suitable, non-human mammalian host in an amount sufficient to induce antibodies to the haptenic analog-ligand.

The antibodies so induced are harvested. The harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand.

Hybridoma cells whose supernatant contains such binding antibodies are then screened to determine which of those cells secreted antibodies that also hydrolyze the substrate enol ester reactant ligand in a manner that yields a product that contains relatively more of one of a pair of enantiomers than the other enantiomer; i.e., the product contains an excess of one enantiomer. Hybridoma cells whose secreted antibodies bind to the immunogen, bind to a substrate enol ester reactant ligand and hydrolyze a substrate enol ester reactant ligand to yield a product that contains relatively more of one of a pair of enantiomers than the other enantiomer are then cloned to provide the desired monoclonal antibodies from culture medium supernatant or from the ascites of a host mammal into which the hybridoma is introduced.

The present invention provides several benefits and advantages One benefit is the preparation of receptors whose binding site topological requirements are tailored to a particular substrate enol ester reactant ligand to be reacted and hydrolyze a preselected bond to yield a product that has an excess of one enantiomer over the other enantiomer.

Another benefit of the present invention is the preparation of receptors that hydrolyze the substrate enol ester reactant ligand at a predetermined site to produce an asymmetric product and that exhibit catalytic properties.

An advantage of the invention is that because of the stereospecificity of the receptors that can be produced, a ligand containing a plurality of different hydrolyzable bonds can be hydrolyzed at a preselected, particular hydrolyzable bond.

Yet another advantage of the present invention is the provision of receptors that can selectively remove a blocking group from an enol ester compound during or after synthesis, thereby facilitating recovery or use, respectively, of a compound that is one of a pair of enantiomers.

Still further benefits and advantages of the present invention will be apparent to those skilled in the art from the discussion that follow

DETAILED DESCRIPTION OF THE INVENTION

I. Introduction

The present invention relates to molecules collectively referred to as receptors that are antibodies or idiotype-containing polyamide (antibody combining site or paratopic) portions induced by an analog of a substrate enol carboxylic ester reactant ligand (usually referred to herein as an enol ester) that mimics the stereochemistry and conformation of the transition state in the reaction sequence for the hydrolysis of that substrate enol ester reactant ligand. The receptor molecules (antibodies and antibody combining sites) that bind to the analog-ligand and to the substrate enol ester reactant ligand are thought to stabilize the hydrolytic transition state of a preselected portion of the substrate enol ester reactant ligand, protect one side of the enol from solvent molecules and protons, and thereby exhibit catalytic properties that produce one enantiomer of the ketone or aldehyde rearranged hydrolysis product of the enol ester reactant ligand in excess over the other enantiomer.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W.P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W.P., *XVII International Solvay Conference (November* 1983)].

The converse proposition is that an antibody that is prepared to optimally bind a suitable analog of a transition state would function as a catalyst. The demonstration of this result by Lerner and co-worker and Schultz and co-workers in the previously cited papers completes the correlation of enzyme function and antibody structure and provides a useful approach to devising artificial enzymes.

The basic idea behind immunological hydrolysis described herein contemplates the use of analog-ligands in the preparation of antibodies of predetermined specificity that preferentially bind to and thereby stabilize the transition state of ester bond hydrolysis upon binding to the specified substrate meso reactant ligand. An analog-ligand simulates the conformation of a high energy transition state in hydrolysis to induce the production of antibodies having the ability to bind related substrates and stabilize their hydrolyses.

Such preferential binding and stabilization results in a reduction in the activation energy for the hydrolysis reaction, thus meeting a criterion for catalysis. Antibodies that display this property can be obtained by immunization with synthetic analogs that are chemically modified to resemble the bonding characteristics of a substrate reactant ligand undergoing bond hydrolysis; i.e., by immunization with transition state analogs of the particular reaction.

In addition, a receptor molecule of the present invention also binds to and hydrolyzes a substrate enol ester reactant ligand to produce an excess of one enantiomeric product over the other. Thus, where the substrate compound is prochiral, the product is a chiral ketone or aldehyde, and one enantiomeric product is present in a greater amount than the other so that an optically inactive prochiral reactant is converted to an optically active, nonracemic product.

The substrate enol ester reactant ligand contains at least one carbon atom that can exist in two stereoisomeric forms after hydrolysis; i.e., one stereoisomeric or prochiral center. The prochiral center is located in the substrate enol ester reactant ligand molecule at the $\beta$-carbon of the enolic unsaturation. Any stereoisomerism provided by the central tetrahedral phosphorus atom of an analog-ligand is not considered herein.

The analog-ligand need not have a stereoisomeric carbon at an analogous position. The only requirement of an analog-ligand is that the antibody combining site (paratope) induced by the analog-ligand encompass both the phosphonate acid moiety, the carbon atom analogous to the $\beta$-carbon of the enolic unsaturation of the substrate ligand and the $C_1$–$C_6$ alkyl group bonded to that $\beta$-carbon atom. In this way, the paratope itself provides the requisite asymmetry to generate a chiral center upon hydrolysis of the prochiral substrate ligand, protonation of the product enolate, and rearrangement of bonds to form a ketone or aldehyde. It is noted that the hydrolysis and protonation steps may be concerted and not stepwise as implied by reciting an enolate product. Whether the mechanism is concerted or stepwise is not of consequence here, and the reaction involved will be usually discussed as if it were stepwise as a matter of convenience of expression.

A receptor molecule of the present invention distinguishes and catalyzes the hydrolysis of a substrate enol ester reactant ligand to produce an asymmetric hydrolyzed derivative of the enol ester reactant ligand; i.e., an aldehyde or lactone. This hydrolysis converts one selected prochiral center into a stereoisomeric center having an R or S configuration.

The above asymmetric induction by catalytic hydrolysis presumes that the locus of asymmetry, the prochiral center, is present in the substrate enol ester reactant ligand near enough to the bond to be hydrolyzed (the scissile ester bond) so that the prochiral center is bound by the catalytic antibody combining site-containing molecule.

The locus of the hydrolyzed bond is determined by the location of the phosphorus atom bonded directly or indirectly to an analogous, pseudoprochiral center of the analog-ligand (and the analogous carbonyl carbon of the scissile ester of the substrate enol reactant ligand) and the size of an antibody combining site. An antibody combining site is normally considered to be able to accommodate about five to about seven amino acid residues.

An analog-ligand itself undergoes no reaction. As such, the analogous site of asymmetry is thus referred to as a pseudoprochiral center in that it never becomes a site of chirality, but is structurally analogous to the prochiral site of the reactant ligand. The prochiral center must, by definition, be on the alcohol portion of the scissile ester bond of the enol ester substrate reactant ligand. The pseudoprochiral center is also located on the alcohol portion of the analog-ligand and is spaced within a distance of two carbons from the oxygen atom of the phosphonate ester that is bonded to the alcohol portion structure of the analog-ligand.

The above chain length distance can readily be determined by use of space-filling models, or where there is doubt, by determining whether a catalytic receptor can hydrolyse a substrate enol ester reactant ligand to perturb the prochiral center to produce relatively more of one of a pair of enantiomers.

In the exemplary catalytic reaction discussed hereinafter, the haptenic analog-ligand is itself pseudoprochiral. The analog-ligand utilized in this exemplary study induced production of receptor molecules that enantioselectively hydrolyzed the substrate enol ester reactant to induce production of an excess of the asymmetric R enantiomeric product. The structures of the analog-ligand and reactant ligand are discussed in detail hereinafter.

The mechanism by which an antibody hydrolyzes an ester bond of a bound reactant ligand can be thought of in terms of an "induced fit" model. As the loosely bound substrate distorts or rearranges to conform to the binding geometry of the antibody, stress can be relieved by chemical reorganization of a single, predetermined ester bond such that this reorganization leads to the hydrolysis of the bond.

The term "receptor" is used herein to mean a biologically active molecule that binds to a reactant ligand, inhibitor ligand, or analog-ligand. The receptor molecules of the present invention are antibodies, substantially intact antibodies or paratope-containing polyamide portions of an antibody.

Biological activity of a receptor molecule is evidenced by the binding of the receptor to its antigenic reactant ligand, inhibitor ligand or analog-ligand upon their admixture in an aqueous medium, at least at physiological pH values and ionic strengths. Preferably, the receptors also bind to an antigenic ligand within a pH value range of about 5 to 9, and at ionic strengths such as that of distilled water to that of about one molar sodium chloride.

Idiotype-containing polyamide portions (antibody combining sites or paratopes) of antibodies are those portions of antibody molecules that include the idiotype, and bind to the ligand or analog-ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [*Science*, 234, 1570 (1987)] Who reported accelerated hydrolytic rates for Fab fragments were the same as those of the native immunoglobulin. Inasmuch as the antibodies from which idiotype-containing polyamides are obtained are described as raised against or induced by immunogens, idiotype-containing polyamide (antibody combining site-containing) receptors are discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors useful in the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies of the present invention are well known. Such receptors were first described by Kohler and Milstein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

A "ligand" is defined herein as a molecule that immunoreacts with or binds to a receptor molecule antibody combining site. Two types of ligand are contemplated herein. A first is termed an analog-ligand and is used as an immunogen (hapten) to induce preparation of receptor molecules and as an inhibitor of the receptor molecule-catalyzed reaction. The analog-ligand is inert to undergoing the catalyzed reaction. The second ligand is referred to as the reactant ligand, substrate ligand or similar phrase and is a prochiral enol ester molecule that undergoes the catalyzed hydrolysis reaction.

As described herein, chemical analogs of prochiral enol ester substrate ligands are synthesized that incorporate phosphonate moieties at specific, predetermined sites to mimic the conformation of the transition state in the hydrolysis of an ester bond. Such analogs are suitable candidates for this investigation because it is known that phosphonamidates have been used as transition state analogs in the inhibition of proteolytic enzymes [Bartlett, et al., *Biochemistry*, 22, 4618 (1983)].

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog-ligand), and recognize and bind not only to that first molecule, but also to an enol ester compound of a second, structurally similar molecule (the prochiral enol ester reactant ligand).

In binding that second molecule, the receptor causes hydrolysis (which as demonstrated herein is catalytic) of a preselected, enol ester bond that corresponds in topology to the topology of the immunizing, haptenic first molecule. The correspondence in topology; i.e., size, shape, stereochemistry and charge, provides a means for preselecting the site at which hydrolysis of the substrate ligand occurs as well as providing a means for perturbing the prochiral center of the enol ester reactant ligand to yield a chiral product that contains relatively more of one of a pair of enantiomers than the other. Inhibitor ligands that resemble the structure of an analog-ligand or an enol ester reactant ligand are also bound by receptor molecules and do not undergo a reaction catalyzed by the receptor.

Consequently, by synthesis of a relatively small, immunizing haptenic analog-ligand, one can induce the production of receptor molecules that recognize, bind to and catalytically cleave an ester bond in another molecule that can contain a plurality of ester bonds. Thus, a receptor can be prepared that causes hydrolysis of a selected, predetermined ester bond of a model enol ester compound and yield a product that contains more of one of a pair of enantiomers than the other.

The implication of this result is that one can confer the activity of hitherto unknown enol esterases to immunoglobulins. Furthermore, the activity of the antibody combining site can be directed to any predetermined site at will by designating the ester bond to be cleaved with the phosphonate configuration in the haptenic analog-ligand used for immunization.

Thus, antibodies and idiotype-containing polyamide portions of antibodies are induced by a haptenic enol ester analog-ligand hydrolytic transition state molecule. The haptenic molecule contains a tetrahedrally bonded central phosphorus atom bonded directly to (a) a carbon atom of the carboxylic acid portion of the analogous enol ester (b) two oxygen atoms and (c) a third oxygen atom that is bonded to a carbon atom (the alpha-carbon) of the alcohol portion of an analogous enol ester of the reactant ligand.

II. Transition State of Esterolysis and Hapten (Analog-Ligand) Design

Design of the analog-ligand flows backward from the structure of the product to be formed through the transition state for bond cleavage to be mimicked, and then to the analog-ligand. Reactions that involve amide or ester hydrolysis provide illustrative examples of the general concept and are utilized herein as exemplary for an ester hydrolysis reaction.

Transacylation processes are characterized by carbonyl addition-elimination mechanisms. The acyl group may, therefore, possess varying degrees of tetrahedral character in this transition state. W. P. Jencks, *Catalysis in Chemistry and Enzymology*, ch. 10, (McGraw-Hill, New York, 1969). The enzymes that catalyze transacylation reactions might be expected to bind well those analogs of the reactant ligand having a tetrahedral configuration about the acyl center. This is true for serine proteases, where a covalent bond between the ligand (substrate) and the enzyme is formed temporarily [Westerik et al., *J. Biol. Chem.*, 247, 8195 (1972); R. C. Thompson, *Biochemistry*, 12, 47 (1973) and Imperali et al., *Biochemistry*, 25, 3760 (1986)], as well as for enzymes that catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*, 103, 654 (1981)].

Naturally occurring and synthetic substances containing phosphorus have been studied as inhibitors of metallopeptidases. In these enzymes, the transition state would appear to contain the hydrated amide in the coordination sphere of the metal ion [W. N. Lipscomb, *Acc. Chem. Res.*, 15, 232 (1982)]. A complete picture of a transition state analog might then have the phosphono group of an inhibitor as a ligand to a metal ion or some other polarizing site [Weaver et al., *J. Mol. Biol.*, 114, 119 (1977) and Christianson et al., *J. Am. Chem. Soc.*, 108, 545 (1986)]. The role of the metal ions in metallopeptidases, however, is not clearly understood. It may have a multiple function in amide hydrolysis where proton transfer steps among the tetrahedral intermediates may be rate-limiting [L. M. Sayre, *J. Am. Chem. Soc.*, 108, 1632 (1986)].

The hydrolysis of carboxylic acid esters is a simpler example of transacylation that should also be approximated by the phosphonate-containing analog of the transition state. The binding of the charged phosphonate group may describe a stabilizing interaction in the transition state that would lead to catalysis. Ester hydrolysis reactions exhibit spontaneous rates under ambient conditions that are suitable for antibodies. Therefore, any small rate acceleration can be readily detected.

The structures of the analog-ligands and reactant ligands for this investigation were selected according to certain criteria. These included the availability and stability of the organophosphorus precursors, the corresponding carboxylic acid substrate, the convenience of the chemical synthesis for its preparation, and the adaptability to diverse schemes of immunological presentation.

The design of the analog ligand was also influenced by the substrate destabilization principle first applied in the design of antibodies with acyl transferase activity [Janda et al., *Tetrahedron,* 47:2503-2506 (1991)]. In those studies, the substrate most structurally congruent to the analog ligand was a poorer substrate for the antibodies than was a substrate that differed by one heteroatom. Despite the weaker binding of the latter substrate, as evidenced by a lower $K_m$, the catalytic activity was higher.

In the present invention, the positioning of the methyl group on the cyclohexyl moiety in analog-ligand Compound A was altered relative to its position on the cyclohexenyl moiety in Compound 1. Both compounds are illustrated hereinafter. This was done in an attempt to increase the catalytic activity of the antibody molecules induced by analog-ligand Compound A in accordance with the substrate destabilization principle. Those two methyl groups are bonded to their respective rings at the pseudoprochiral center and prochiral center, respectively.

As has already been noted, a substrate or reactant ligand useful herein is an enol carboxylic ester or enol ester. As such, a substrate ligand contains ethylenic unsaturation or a vinyl group. One carbon atom of that vinyl group, the α-carbon, is bonded to an oxygen atom, thereby defining the enol group. That oxygen is bonded to the acyl portion of the molecule, thereby constituting an ester bond.

That ester bond is cleavable or scissle. Hydrolysis of the ester bond and protonation of the resulting enolate anion, presuming a stepwise reaction, forms an enol. Enols are themselves unstable and rearrange spontaneously to a corresponding ketone or aldehyde.

The β-carbon atom of the above vinyl group or ethylenic unsaturation is bonded to a $C_1$-$C_6$ alkyl group. That β-carbon atom, because of its bonded $C_1$-$C_6$ alkyl group constitutes a prochiral center. Thus, aside from any other chiral center present in a substrate or reactant ligand, the β-carbon atom of the vinyl group, which is not chiral in the enol ester, becomes chiral after hydrolysis, protonation and rearrangement to an aldehyde or ketone. Inasmuch as the β-carbon atom can become chiral, it is referred to as being a prochiral center.

A substrate ligand of the present invention can be depicted by structural Formula I.

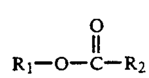

I wherein $R_1$ is an alkenyl or cycloalkenyl group that contains at least 5 carbon atoms and a prochiral center, and more preferably 6 to about 10 carbon atoms and attendant hydrogens. The α-carbon of the ethylenic unsaturation is bonded directly to the oxygen atom of the ester linkage, thereby defining the enolic portion of the ester. The β-carbon atom of the ethylenic unsaturation is bonded to a $C_1$-$C_6$ alkyl (methyl, ethyl, iso-propyl, sec-butyl, cyclopentyl, hexyl, cyclohexyl or the like), thereby defining the prochiral center.

An $R_1$ group can be a straight or branched alkenyl or cycloalkenyl group. Exemplary groups include heptenyl, 1-methylpentenyl, 1-methyl-1,3-butadienyl, 2-methylbutenyl, cyclopentenyl, and 1,6-cyclooctadienyl, and the like.

An $R^2$ group can be a straight, branched or cyclic alkyl group and can contain one to about 10 carbon atoms, and preferably about 6 to about 10 carbon atoms. Exemplary alkyl groups include methyl, ethyl, isopropyl, allyl, t-butyl, pentyl, cyclopentyl, cyclohexyl, cyclohexenyl, 2-methylpentyl, hexyl, heptyl, octyl, nonyl, decyl, and the like. An $R^2$ group can also be an aromatic radical such as phenyl, m-toluyl, naphthyl, xylyl, and the like. Aralkyl radicals such as benzyl, phenethyl, p-methylbenzyl, and the like are also contemplated $R^2$ groups.

At least one of $R_1$ and $R_2$, and preferably both, contain a ring structure having 5 to 7 carbon atoms in the ring. Exemplary ring structures for both $R_1$ and $R_2$ are noted above.

An exemplary enol ester substrate ligand utilized herein is 1-phenylacetoxy-2-methycyclohexene (Compound 1), whose structure is illustrated below.

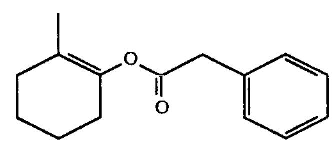

1

Using structural Formula I as a guide, an analog-ligand corresponds to structural Formula II, below.

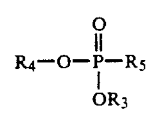

II wherein $R_4$ is structurally analogous to $R_1$ except that $R_4$ is saturated at positions analogous to the enolic unsaturation of $R_1$, and $R_4$ is bonded to the phosphonate ester oxygen at a position isomeric to the α-carbon atom of the $R_1$ enolic saturation, but within a distance of two carbon atoms thereof;

$R_5$ is structurally analogous to $R_2$, except that an $R_5$ group of an analog-ligand further includes a group or radical through which a haptenic analog-ligand can be linked to an antigenic carrier for purposes of immunization, as noted hereinafter; and $R_3$ is H (hydrogen), $C_1$-$C_4$ alkyl, benzyl or an alkali metal salt.

$R_4$ is structurally analogous to $R_1$ and $R_5$ is structurally analogous to $R_2$, with certain exceptions. Keeping those exceptions in mind, where $R_1$ includes a 6-membered ring or a straight chain, so does $R_4$, and where $R_2$ includes a phenyl ring so does $R_5$. Thus, but for the noted exceptions, $R_4$ and $R_1$ can be otherwise identical, as can $R_2$ and $R_5$.

Structural identities but for the noted exceptions are not required, however, and some leeway can be given from structural congruity (identity) between the reactant and analog-ligands. Thus, for example, the size of the alkyl group constituting the pseudoprochiral center can be larger than the alkyl group of the prochiral center, e.g. butyl vs. ethyl, respectively. An analog-ligand can also include more or less ethylenic unsaturation than the reactant ligand.

Exemplary further $R_1$—O and $R_4$—O groups of Formula I (substrate ligand) and Formula II analog ligand) are shown below.

| $R_1$ Group of a Substrate Ligand | $R_4$ Group of an Analog-Ligand |
|---|---|
| (cyclopentenyl-O) | (cyclopentyl-O) |
| (octahydronaphthalenyl-O) | (decahydronaphthalenyl-O) |
| HC=O<br>H₃C—C<br>CH₂<br>CH₂<br>CH₃ | H₂C—O<br>CH₃—CH₂—C<br>CH₂<br>CH₂<br>CH₃ |

It should also be apparent from structural Formula II that only one phosphonate ester is present in an analog-ligand.

By including an additional carboxylic acid, mercaptan or amine substituent in the $R_5$ portion of the analog-ligand as in the acid portion of Compound A (below), the analog-ligand can be provided with a functional appendage for coupling to an antigenic (immunogenic) carrier protein. Such an added appendage is useful where the analog-ligand is a hapten, as is typically the case. The appendage and accompanying linking atoms can also be present in the reactant ligand, particularly where the reactant ligand is relatively small so that the antibody combining site can be relatively filled with the ligand.

An analog-ligand that provides the necessary features for asymmetric induction by catalytic hydrolysis is the 1-methylcycloheane ester analog ligand, Compound A, that is shown below.

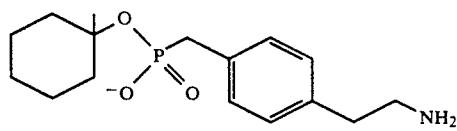

A

Compound A is shown in its haptenic form prior to coupling to a linking group and an antigenic carrier for immunization.

Thus, the present invention generally relates to monoclonal receptors that catalytically hydrolyze a preselected ester bond of a substrate prochiral enol ester reactant ligand to form a chiral product having an excess of one enantiomer. The receptors contain an antibody combining site that binds: (a) to and catalyzes the hydrolysis of an enol ester reactant ligand containing at least five carbon atoms that can form the tetrahedral hydrolytic transition state of a preselected ester bond of the reactant; i.e., contains a preselected scissile enol carboxylic acid ester bond, and including a prochiral center, and (b) to and is induced by an analog-ligand that has a tetrahedrally bonded phosphorus atom located at the position occupied by the carbonyl carbon atom of the preselected scissile ester bond of the enol ester reactant ligand substrate. The tetrahedrally bonded phosphorus atom is bonded directly to:

(i) a carbon atom (the alpha-carbon) of the acid portion of the analogous enol ester reactant ligand ester that is included in a radical chain that contains at least one carbon atom, and more preferably contains 6 to about 10 carbon atoms and attendant hydrogen atoms;

(ii) two oxygen atoms, one of which is bonded to the phosphorus atom by a double bond whereby the oxygen is an oxo radical, and the other of the two oxygen atoms is bonded singly to the phosphorus and is also bonded to a hydrogen, a $C_1$-$C_4$ alkyl or benzyl radical or is an oxy group (O) neutralized by an alkali metal cation;

(iii) a third oxygen atom that is bonded to a carbon atom of the alcohol portion of the analogous ester; i.e., to the alpha-carbon of the alcohol portion of the ester, that is a portion of a radical that contains at least five carbon atoms, and more preferably contains six to about ten carbon atoms, along with attendant hydrogen atoms.

An enol ester substrate ligand can be prepared by straight forward procedures for esterification. Such methods include reaction of a ketone or aldehyde with one mole or more of an acid halide or anhydride.

Preparation of the analog-ligand is somewhat more complex, but is nevertheless also relatively straight forward. An exemplary synthesis of an enol ester analog-ligand is provided hereinafter. Further syntheses of phosphonate derivatives that provide additional phosphorus-containing analogs of hydrolytic ester transition states can be found in U.S. Pat. Nos. 4,659,567 and 5,030,717, whose disclosures are incorporated by reference.

In a more general reaction, a tri $C_1$-$C_4$ alkyl phosphite is reacted with an appropriate alkyl halide such as a bromide to provide a dialkyl phosphonate ester. Reaction with oxalyl chloride forms a phosphonochloridate methyl ester. The latter compound is reacted with the alcohol portion in the presence of a non-nucleophilic strong base such as lithium diisopropylamide to form the analog-ligand as a monomethyl phosphonate ester. The monomethyl phosphonate ester is removed by treatment with a tempered amine such as tert-butylamine to provide a hydroxyl group salt, that can be neutralized with an acid such as hydrochloric acid that can also be exchanged to form a salt with an alkali metal hydroxide if desired.

The mono $C_1$-$C_4$ alkyl phosphonate ester group can also be removed by treatment with trimethylsilylbromide in chloroform. Exemplary $C_1$-$C_4$ alkyl groups of phosphonate ester include methyl, ethyl, isopropyl and butyl. Methyl is preferred.

As is noted elsewhere, the analog-ligand typically includes a group that is utilized to link the haptenic small molecule to an antigenic carrier molecule to form an immunogenic conjugate. That linking group is a part of the acid portion of the molecule, as compared to the portion analogous to the enolic portion.

As a consequence of the requirements for immunization, the structure of an analog-ligand is analogous and not congruent with the structure of a substrate ligand. That lack of structural congruence includes the replacement of the carbonyl carbon atom of the scissile ester bond with the tetrahedral phosphorus atom as already discussed, the absence of ethylenic unsaturation in the analog-ligand, the placement of the prochiral and pseudoprochiral centers and inclusion of the group used for linking to the antigenic carrier. Regardless of that lack of structural congruity, the substrate and immunizing ligands are structurally similar enough (analogs of each other) so that the induced antibody molecules bind to both.

An inhibitor ligand is also often used when studying the properties of a catalytic receptor. An inhibitor ligand is typically identical to an analog-ligand except that a linking group that would have an ionic charge in water at the pH values of the study is sometimes made to be free of ionic charge. For example, where the linking group of the analog-ligand is a carboxylic acid, the corresponding inhibitor ligand contains an ester or amide group of that carboxylic acid. Similarly, if the linking group is an amine, the inhibitor can have an amide prepared from that amine. The inhibitor ligand is preferably free from ionic charge so that it more closely resembles the substrate ligand that is also free of ionic charge. In the present studies, Compound A, which bears an ionic charge at the pH values studied, was used as the inhibitor.

In another embodiment, this invention relates to a method of catalytically hydrolyzing a preselected ester bond in an enol ester reactant ligand molecule to yield a product that is in enantiomeric excess; i.e., one of two enantiomeric aldehydes or ketones is produced in a relatively larger amount than the other enantiomer. The enantiomeric excess can be as small as one to five percent, and is preferably about 30 percent or more up to complete enantiomeric purity. The method comprises the steps of: (a) admixing a catalytically effective amount of one of the foregoing receptors with enol ester reactant ligand molecules that contain a prochiral center in an aqueous medium; and (b) maintaining the admixture for a period of time sufficient for the enol ester reaction ligand molecules to bind to the receptors and for the receptor molecules to hydrolyze the preselected bond of the enol ester reactant ligand to yield a product that is in enantiomeric excess. The aldehyde or ketone product of that hydrolysis can be thereafter recovered, if desired.

A hydrolytic method of this invention utilizes an aqueous medium as a portion of the reaction admixture. That medium typically contains water and buffer salts. In addition, the medium can contain other salts such as sodium chloride, as well as water-soluble calcium and magnesium salts as are frequently found in protein-containing media. Organic solvents such as methanol, ethanol, acetonitrile, dimethyl sulfoxide, dioxane, hexamethylphosphoramide and N,N-dimethylforamide can also be present. Surface active agents that emulsify the reactant ligand and receptor molecule can also be present. The critical feature of ingredients present in the aqueous medium is that those ingredients not substantially interfere with or inhibit the catalytic reaction as by denaturation of the receptor molecule. Additionally, the aqueous medium is substantially free from salt, proteins generally, and enzymes, specifically, that inhibit the bond-breaking reaction catalyzed by the receptor molecule.

The aqueous medium typically has a pH value of about 5 to about 9, and preferably about pH 6.0 to about 8.0. pH Values greater and less than those recited values can also be utilized so long as the catalyzed reaction is again not substantially interfered with or inhibited.

The catalytic reactions are typically carried out at ambient room temperature; i.e., at about 20 to about 25° C. or at 37° C., and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g., at about 100° C. and thus temperatures below about 40° C. are preferred. As is also well known, reactions that follow multimolecular kinetic expressions decrease in rate as the temperature decreases. Thus, a minimal temperature of about 15° C. is preferred.

The reactant ligand is present in a reaction mixture in an amount up to its solubility in the aqueous medium. A two phase system that includes insoluble reactant ligand can also be used, but normally is not so used. Normally used concentrations of the reactant ligand are about 0.1 micromolar ($\mu$M) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studied.

An effective amount of the receptor molecule is also present. That effective amount is typically a catalytic amount; i.e., the receptor is used at a molar ratio to the reactant ligand of about 1:2 to about 1:10,000, with a molar ratio of about 1 10 to about 1:100 being preferred. The ratio of receptor molecule to reactant ligand typically depends upon the specific activity of the receptor molecule toward the reactant ligand and the purpose of the user in running the reaction.

Thus, where the product is desired, a relatively higher concentration of receptor an higher receptor to reactant ligand ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The admixture formed from mixing receptor molecules and reactant ligand molecules in an aqueous medium is maintained for a time period sufficient for the binding and reaction to occur. The duration of that maintenance period is a function of several parameters including the receptor and reactant ligand selected, their concentrations, pH value, and temperature, as well as what is being sought from the reaction.

Thus, where kinetic studies are being carried out, maintenance times of minutes to hours are frequently encountered. Where the reaction products are desired, maintenance times of hours to days are more usual.

III. Results

The enantiomeric Compound A covalently linked to KLH was used as an immunogenic conjugate to immunize mice. Hybridomas were prepared using spleen cells from an immunized animal. The synthesis of Compound A (shown before), as well as the intermediates in its synthesis are discussed hereinafter.

Twenty-six hybridomas were prepared whose secreted monoclonal antibodies (receptors) bound to Compound A. Of those twenty-six monoclonals, three monoclonal receptors were capable of catalytically hydrolyzing the exemplary enol ester reactant (substrate) ligand Compound 1 and were of the IgG isotype. The specific conditions used for the stereoselective hydrolyses are discussed hereinafter.

The monoclonal antibody-mediated hydrolysis of the enol ester Compound 1 to form (2R)-methylcyclohexanone (Compound 2) is shown below wherein the star (*) indicates the chiral center:

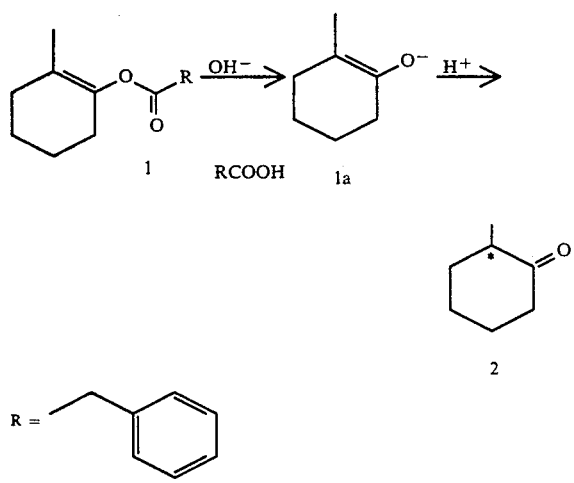

The production of Compound 2 by a monoclonal antibody composition of this invention was assayed at a concentration of 20 µM monoclonal antibody and 1.5 mM Compound 1 in 10 percent dimethylsulfoxide (DMSO)/ATE buffer (0.52M ACES, 0.52M Tris, 0.01M ethanolamine pH 9.0) at 25° C. The initial rate of hydrolysis of Compound 1 by the monoclonal antibodies produced by three hybridomas followed Michaelis-Menten kinetics (Table 1 hereinafter).

Inasmuch as the monoclonal antibodies were induced by Compound A, addition of free Compound A to a hydrolysis reaction catalyzed by the monoclonal antibodies of this invention should cause extensive inhibition. Table 1 shows that addition of free Compound A caused extensive inhibition of the hydrolytic reaction caused by all three monoclonal antibodies as indicated by the $K_I$ values.

TABLE 1

Kinetic Parameters of Hydrolysis of Compound 1[a]

| Antibody Source | $K_m$ ($\times 10^{-6}$M) | $K_{Cat}$ (min$^{-1}$) | $K_i$ ($\times 10^{-6}$M) |
|---|---|---|---|
| Hydridoma 27B5 | 994 | 0.01 | 4.3 |
| Hybridoma 7F9 | 909 | 0.02 | 6.5 |
| Hybridoma 32B11 | 830 | 0.01 | 15.2 |

[a]Hydrolysis rates were measured by following the generation of phenylacetic acid via HPLC on a RP-C18 column eluting with water-acetonitrile (85:15) at a flow rate of 1 ml/minute with UV detection at 260 nm.

The ability of a monoclonal antibody composition produced by hybridoma 27B5 to hydrolyze enol ester Compound 1 to yield a product that Was in enantiomeric excess (Compound 2) was investigated by gas chromatographic analysis of a reaction of each of the three monoclonal antibodies (20 µM) in 10 percent DMSO/ATE buffer, containing 500 µM Compound 1. When 70 µM of product Compound 2 was produced, the assay mixture was extracted with diethyl ether, concentrated, and injected into a microcapillary gas chromatography column (Chrompack, CD-(optically pure)-Cyclodextran-B-236-M-19).

Although all three monoclonal antibodies hydrolyzed Compound 1, only one, produced by hybridoma 27B5 and designated the same, yielded the R enantiomer of Compound 2 in excess of five percent over the S enantiomer. Specifically, monoclonal antibody 27B5 produced the R-enantiomer in excess of 42 percent. No racemization of Compound 2 was observed when its S-enantiomer was allowed to stand overnight.

No asymmetric induction was detected when racemic Compound 2 (50 µM) was incubated with antibody 27B5 (50 µM). This result rules out the possibility that antibody 27B5 binds the S-enantiomer of racemic product Compound 2 to generate the enantiomeric excess.

It is believed that the above-described catalytic hydrolyses are the first such asymmetrically induced hydrolysis ever reported. It is further believed that this is the first report of the preparation of antibody combining site-containing receptor molecules that can catalyze a reaction of an enol ester compound to yield relatively more of one enantiomer than the other.

Mechanistically, hydrolysis of enol ester Compound 1 was anticipated to proceed through a water or hydroxide mediated process, which was approximated using the phosphonate moiety as a transition state analog. That hydroxide ion mediates the hydrolysis is suggested by the reaction's linear dependence on hydroxide ion concentration in the range of pH 7.5-10.

The mode of protonation of the enol fragment remains undetermined. Thus, although it is thought that a stepwise process is involved (enol/enolate), a concerted hydrolysis-protonation mechanism cannot be ruled out.

Because the hapten has no bias towards induction of amino acid residues in the antibody binding pocket capable of proton donation, it is thought that the receptor-mediated process provides enantiofacial discrimination through inaccessibility of solvent to one face (side) over the other. This hypothesis suggests that the illustrated imperfect receptor-mediated enantiospecificity is due to insufficient antibody binding, and therefore incomplete proton transfer within the active site. Tighter binding of the substrate ligand to the antibody combining site, as by closer structural congruence between the hapten analog-ligand and substrate is thought to enhance the enantiofacial protonation of one side of the enolate over the other.

IV. Preparation of Analog-Ligands

It is noted that the syntheses discussed hereinbelow relate only to one enol carboxylic ester as reactant ligand and one phosphonate as analog ligand. However, those syntheses can be readily adapted for the preparation of different enol ester and phosphonate compounds by simple substitutions of reactants.

The synthesis of analog ligand Compound A was accomplished using the Michaelis-Becker reaction. The phosphite and alkyl bromide required for the reaction were prepared as follows. To a solution of phosphorus trichloride (1.0 equivalent) in dry benzene was added a mixture of benzyl alcohol (0.8 equivalents) and pyridine (0.8 equivalents) dropwise at room temperature. After eight hours, a mixture of 1-methylcyclohexanol (0.8 equivalents) and pyridine (0.8 equivalents) was added and the reaction mixture stirred about 18 hours (overnight). The resulting solution was treated via aqueous workup and purified by flash chromatography (50/50 ethyl acetate/hexane; Rf=0.31) to give 1-methylcyclohexyl benzyl phosphite (28 percent yield).

That disubstituted phosphite was reacted with 4-(2-benzyloxycarbonyl)aminoethylbenzyl bromide, which was prepared from 4-(2-aminoethyl)benzyl alcohol via protection of the amino group (ClCO$_2$CH$_3$Ph/NaHCO$_3$/H$_2$O) followed by bromination (Br$_2$PPh$_3$/CH$_4$CN), in the presence of sodium hydride in dry tetrahydrofuran to afford the protected phosphonate. Deprotection of both benzyl groups [H$_2$,Pd(OH)$_2$-C/MeOH] provided phosphonate Compound A. Compound A was coupled with activated linker (N-hydroxy succinimidyl glutaryl chloride) to provide hapten Compound A1, which Was purified by high pressure liquid chromatography on a RP-C18 column eluting with 90/10 H$_2$O (0.1 percent TFA)/CH$_4$CN (retention time=17 minutes). All new compounds gave satisfactory spectroscopic data (NMR,IR) and combustion analyses (±0.3 percent).

V. Preparation of Conjugates and Inocula

Conjugates of haptenic analog-ligand molecules with antigenic (immunogenic) protein carriers such as keyhole limpet hemocyanin (KLH) can be prepared, for example, by activation of the carrier with a coupling agent such as MBS (m-maleimidobenzoyl-N-hydroxy succinimide ester), and coupling to the thiol group of the analog-ligand. See, for example, Liu et at., *Biochem.*, 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

In an exemplary procedure, 2.5 mg of a reaction product of haptenic analog-ligand containing an added alcohol or amine group for linking purposes and succinimidyl adipoyl chloride or succinimidyl glutaroyl chloride in 250 μl of dimethylformamide is slowly added to 2 mg of KLH in 750 μl of 0.01M sodium phosphate buffer at a pH value of 7.2. A temperature of 4° C. is utilized and the resulting admixture is stirred for about one hour to form the hapten-linked KLH conjugate. The conjugate reaction product so formed is thereafter purified by usual means.

In the present work Compound A1 (2 mg) was admixed with KLH (2 mg) in water (2 ml). The pH was adjusted to 4.5 with HCl and 10 equivalents of 1-ethyl-3-(3-dimethylaminopropyl)-carbodiimide were then added. The mixture was stirred for about 12 hours. The resultant crude product was injected into mice.

VI. Preparation of Monoclonal Receptors

The foregoing KLH conjugates (about 100 μg) were used to immunize mice (129G1X* strain), and monoclonal antibodies were obtained as described by Niman et al., *Proc. Natl. Acad. Sci. USA*, 77, 4524 (1980) and Niman et al., in *Monoclonal Antibodies and T-Cell Products*, Katz, D. H. ed., 23–51, CRC. Press, Boca Raton, Fla. (1982). The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog-ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al., eds., John Wiley & Sons Ltd., p. 273 (1982)]. Suitable myeloma lines for use in the present invention include MPC-11 (ATCC. CRL 167), P3X63-Ag8.653 (ATCC. CRL 1580), Sp2/0-Ag14 (ATCC CRL 1581), P3X63Ag8U.1 (ATCC. CRL 1597), Y3-Agl.2.3. (deposited at Collection Nationale de Cultures de Microorganisms, Paris, France, number I-078) and P3X63Ag8 (ATCC. TIB 9). The non-secreting murine myeloma line Sp2/O or Sp2/O-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X* mice bred in the mouse colony of The Scripps Research Institute, La Jolla, Calif.; however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975) and Engvall, E., *Methods Enzymol.*, 70, 419 (1980). Specifically, female 129GIX* mice were immunized by intraperitoneal injection with an inoculum of 100 micrograms of conjugate (e.g., Compound A1 bound to KLH) in 300 microliters of a 1:1 mixture of phosphate buffered saline (PBS), pH 7.4, and complete Freund's adjuvant. Two weeks later, the mice were again injected in a like manner with 50 micrograms of the foregoing conjugate in 300 microliters of a 1:1 mixture of PBS (pH 7.4) and 10 mg/ml alum. After an additional eight weeks, the mice were immunized intravenously with 50 micrograms of the conjugate in 200 microliters of PBS (pH 7.4). The spleens were removed from the mice four days later, and the spleen cells were fused to myeloma cells.

The spleens cells were pooled and a single cell suspension was made. Nucleated spleen cells ($1.4 \times 10^8$) were then fused with $3 \times 10^7$ Sp2/0-Ag14 nonsecreting myeloma cells in the presence of a cell fusion promoter (polyethylene glycol 2000). A hybridoma that produces a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCA), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound A. Positive wells were cloned twice by limiting dilution. Those clones that continued to produce Compound A-specific antibody after two clonings were expanded to produce larger volumes of supernatant fluid. The hybridoma and the monoclonal receptors produced therefrom and described herein are identified by the laboratory designation as discussed hereinafter.

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse.

Although the host mice also have normal receptors in their blood and ascites, the concentration of normal receptors is typically only about five percent that of the monoclonal receptor concentration.

Monoclonal receptors are precipitated from the ascitic fluids, purified by anion exchange chromatography, and dialyzed against three different buffers.

The abundance of acetyl and butyl cholinesterase in red blood cells and serum [Stedman et al., *Biochem. J.* 26: 2056 (1932); Alles et al., *Biol. Chem.*, 133: 375 (1940)] necessitated extra caution during purification of the antibody molecules. In the present study, IgG molecules were typically obtained from mouse ascites fluid via anion-exchange chromatography on a DEAE Sepharose column followed by affinity chromatography on a Protein G Sepharose column and then again by anion exchange chromatography on a Mono Q column. As a control, authentic acetyl and butyl cholinesterases were not retained in the affinity column when fractionated under the same conditions employed for antibody purification.

Antibodies obtained were judged to be greater than 95 percent homogeneous by sodium dodecyl sulfate polyacrylamide gel electrophoresis [Laemmli, V. *Nature*, 227: 680 (1970)]. The resulting concentrated solutions containing isolated IgG fractions were typically prepared into stock solutions of receptor at 1-20 mg/ml using an appropriate buffer such as 50 mM Tris-HCl or sodium phosphate containing 0.01M sodium azide.

Of twenty-six anti-Compound A monoclonal receptors, one of the IgG isotype catalyzed the hydrolysis of substrate enol ester Compound 1 to yield a product in enantiomeric excess of more than about five percent. The hybridoma that produces the catalytic monoclonal receptor, given laboratory designation 27B5, was deposited at the American Type Culture Collection, 12301 Parklawn Drive, Rockville, Md. on Oct. 8, 1991 and was given ATCC. accession number HB10892.

The present deposit was made in compliance with the Budapest Treaty requirements that the duration of the deposit should be for 30 years from the date of deposit or for five years after the last request for the deposit at the depository or for the enforceable life of a U.S. patent that matures from this application, whichever is longer. The hybridoma will be replenished should it become non-viable at the depository.

A Fab fragment of a monoclonal receptor can be prepared from the purified receptor using predigested papain in a 0.1M sodium acetate buffer, at a pH value of 5.5, at 37° C., followed by reaction with iodoacetamide. The Fab fragment is typically further purified by anion exchange chromatography, dialysis, and DEAE anion exchange chromatography, and its homogeneity is judged by gel electrophoresis.

VII. Enzyme-linked Immunosorbent Assay (ELISA)

The binding of an analog-ligand by the induced monoclonal receptor molecule was assayed by ELISA with antibody at a fixed concentration in the range of its titer and varying inhibitor (free Compound A) concentration. Use of free Compound A as inhibitor helps to assure that an observed binding interaction is antigen-specific.

Assays were performed in flat-bottom polyvinyl microtiter plates (Dynatech, Alexandria, VA). Illustratively, the wells were coated with a solution comprising Compound A1 bonded to BSA (as it was bonded to KLH) as the antigen ligand in phosphate buffered saline (PBS) using 50 microliters of solution per well. BSA was used as a carrier to bind the hapten to the cell wall, and an analog-ligand/BSA conjugate was used in place of the immunizing KLH-containing conjugate to screen out possible anti-KLH antibodies.

The bound ligands were coated at 1 microgram per milliliter. The plates were then incubated overnight at 37° C. in a dry oven. The dried plates were stored at 4° C. until use. Prior to the ELISA assay, dried plates were rehydrated by two washes of two minutes each with ten millimolar (mM) PBS, pH 7.4, containing 0.1 percent polyethylene sorbitan monolaureate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for one hour at 4° C. on a gyroshaker to contact the monoclonal antibody-containing supernatant with the bound Compound A1. Following two washes of two minutes each, 50 microliters of peroxidase-labeled goat anti-mouse IgG+IgM (Tago, Burlingame, Calif.), diluted 1:1000, were added to each well, and the reaction mixture was incubated at 4° C. for one hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of four molar $H_2SO_4$ to each well and the optical density at 492 nanometers (nm) was measured with a Multiskan ELISA plate reader.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., N.Y., 1982; *DNA Cloning*, Glover, ed., IRL Press, McLean VA (1985). For the genomic cloning and expression of immunoglobulin genes in lymphoid cells, see Neuberger et al., *Nature*, 312:604-8 (1984); Ochi et al., *Proc. Natl. Acad. Sci. USA*, 80:6351-55 (1987); and Oi et al., *Proc Natl. Acad. Sci. USA*, 80:825-29 (1983). For cloning of immunoglobulin genes from hybridoma cells and expression in Xenoous oocytes, see Roberts et al., *Protein Engineering*, 1:59-65 (1986), and see Wood et al. for expression in yeast. *Nature*, 314:446-9 (1985).

The foregoing is intended as illustrative of the present invention but not limiting. Numerous variations and modifications can be effected without departing from the true spirit and scope of the invention.

What is claimed is:

1. Monoclonal antibody molecules or paratope-containing portions thereof that catalytically hydrolyze a preselected carboxylic ester bond of a substrate enol ester reactant ligand to yield a product containing relatively more of one of a pair of enantiomers than the other enantiomer, said paratope binding to:

(a) an enol ester substrate ligand having the structural formula:

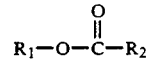

wherein
    $R_1$ is an alkenyl or cycloalkenyl group containing at least 5 carbon atoms and a prochiral center, with the α-carbon atom of the ethylenic unsaturation bonded directly to the oxygen atom of the illustrated ester linkage, thereby constituting the enolic portion of the ester, and the β-carbon of the ethylenic unsaturation bonded to a $C_1$-$C_6$ alkyl group defining the β-carbon as the prochiral center;

$R_2$ is an alkyl, aralkyl or aromatic radical containing at least 1 carbon atom; and at least one of $R_1$ and $R_2$ containing a ring structure having five to seven carbon atoms in the ring; and (b) an analog-ligand of said enol ester reactant ligand having the structural formula:

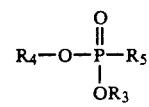

wherein $R_4$ is structurally analogous to $R_1$ except that $R_4$ is saturated at positions analogous to the enolic unsaturation of $R_1$, contains a pseudoprochiral center structurally analogous to said prochiral center, and $R_4$ is bonded to the phosphonate ester oxygen at a position other than at a position analogous to said α-carbon atom and within 2 carbon atoms of said pseudoprochiral center;

$R_5$ is structurally analogous to $R_2$, except that an $R_5$ group of an analog-ligand further includes a group or radical through which said analog-ligand can be linked to an antigenic carrier for purposes of immunization; and $R_3$ is hydrogen, $C_1$-$C_4$ alkyl, benzyl or an alkali metal salt.

2. The monoclonal molecules of claim 1 secreted by the hybridoma 27B5 having ATCC accession number HB10892.

3. The monoclonal molecules of claim 1 wherein said enol ester substrate ligand has the formula

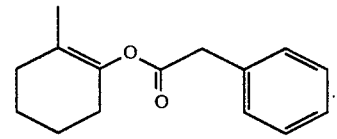

4. A hybridoma that secretes a monoclonal antibody molecule containing a paratope that catalytically hydrolyzes a preselected scissile carboxylic acid ester bond of a substrate enol ester reactant ligand containing a prochiral center to yield a product that contains relatively more of one of a pair of enantiomers than the other enantiomer, said paratope binding to:

(a) an enol ester substrate ligand having the structural formula:

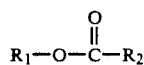

wherein
    $R_1$ is an alkenyl or cycloalkenyl group containing at least 5 carbon atoms and a prochiral center, with the α-carbon atom of the ethylenic unsaturation bonded directly to the oxygen atom of the illustrated ester linkage, thereby constituting the enolic portion of the ester, an the β-carbon of the ethylenic unsaturation bonded to a $C_1$-$C_6$ alkyl group defining the β-carbon as the prochiral center;

$R_2$ is an alkyl, aralkyl or aromatic radical containing at least 1 carbon atom; and at least one of $R_1$ and $R_2$ containing a ring structure having five to seven carbon atoms in the ring; and (b) an analog-ligand of said enol ester reactant ligand having the structural formula:

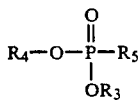

wherein $R_4$ is structurally analogous to $R_1$ except that $R_4$ is saturated at positions analogous to the enolic unsaturation of $R_1$, contains a pseudoprochiral center structurally analogous to said prochiral center, and $R_4$ is bonded to the phosphonate ester oxygen at a position other than at a position analogous to said α-carbon atom and within 2 carbon atoms of said pseudoprochiral center;

$R_5$ is structurally analogous to $R_2$, except that an $R_5$ group of an analog-ligand further includes a group or radical through which said analog-ligand can be linked to an antigenic carrier for purposes of immunization; and $R_3$ is hydrogen, $C_1$-$C_4$ alkyl, benzyl or an alkali metal salt.

5. The hybridoma of claim 4 designated 27B5 and having the ATCC accession number HB10892.

6. A method of catalytically hydrolyzing a preselected carboxylic ester bond of a substrate enol ester reactant ligand comprising the steps of:

(a) admixing a catalytically effective amount of the monoclonal antibody molecules or paratope-containing portions thereof of claim 1 with said substrate enol ester reactant ligand molecules in an aqueous medium to form an admixture; and (b) maintaining said admixture for a period of time sufficient for said substrate enol ester reactant ligand molecules to bind to said monoclonal antibody or paratope-containing portions thereof and for said monoclonal antibody molecules or paratope-containing portions thereof to hydrolyze said preselected scissile carboxylic ester bond to yield a product that contains relatively more of one of a pair of enantiomers than the other enantiomer.

7. The method of claim 6 wherein $R_1$ has the formula:

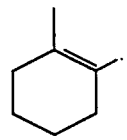

8. The method of claim 7 wherein $R_2$ has the formula:

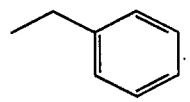

* * * * *